US008568376B2

(12) United States Patent
Delattre et al.

(10) Patent No.: US 8,568,376 B2
(45) Date of Patent: *Oct. 29, 2013

(54) INCONTINENCE DEVICE FOR AMBULATORY MALES (75) Inventors: Thomas Delattre, Stuart, FL (US); David Carson, Stuart, FL (US)

(73) Assignee: Envision Product Development Group, Stuart, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/269,253

(22) Filed: Oct. 7, 2011

(65) Prior Publication Data

US 2013/0090621 A1    Apr. 11, 2013

(51) Int. Cl.
*A61F 13/45* (2006.01)
(52) U.S. Cl.
USPC .................................... 604/385.01
(58) Field of Classification Search
USPC ............... 604/385.01, 327, 347, 349, 353, 604/350–352, 385.04, 393, 395, 400, 402, 604/385.09, 385.19
See application file for complete search history.

(56) References Cited

U.S. PATENT DOCUMENTS

| 2,439,683 | A | * | 4/1948 | Broderick | 604/353 |
| 2,798,484 | A | * | 7/1957 | Boudreaux | 602/70 |
| 4,627,846 | A | | 12/1986 | Ternstrom | |
| 4,710,188 | A | | 12/1987 | Runeman | |
| 5,275,592 | A | | 1/1994 | Grizzaffi | |
| 5,618,279 | A | | 4/1997 | Pudlo | |
| 5,669,901 | A | | 9/1997 | LaFortune et al. | |
| 5,716,350 | A | * | 2/1998 | Ryan | 604/385.09 |
| 5,722,968 | A | | 3/1998 | Datta et al. | |
| 5,984,910 | A | | 11/1999 | Berke | |
| 6,059,762 | A | * | 5/2000 | Boyer et al. | 604/349 |
| 6,248,096 | B1 | | 6/2001 | Dwork et al. | |
| 6,443,930 | B1 | | 9/2002 | Silverstein | |
| 6,508,794 | B1 | | 1/2003 | Palumbo et al. | |
| 6,569,135 | B1 | | 5/2003 | Mula | |
| 6,635,038 | B2 | | 10/2003 | Scovel | |
| 7,066,920 | B1 | | 6/2006 | Mula | |
| 7,104,976 | B1 | | 9/2006 | Allen, Sr. | |
| RE39,371 | E | | 10/2006 | Johnson | |
| 7,125,399 | B2 | | 10/2006 | Miskie | |
| 7,658,730 | B2 | | 2/2010 | Conley | |
| 7,789,868 | B2 | | 9/2010 | Tachibana | |

(Continued)

FOREIGN PATENT DOCUMENTS

GB            2106395 A      4/1983

*Primary Examiner* — Elizabeth Houston
*Assistant Examiner* — Mark Wardas
(74) *Attorney, Agent, or Firm* — Duane Morris LLP; J. Rodman Steele, Jr.; Gregory M. Lefkowitz (57) ABSTRACT

A disposable absorbent device for collecting urine from an individual is disclosed. The disposable absorbent device can include an absorbent body, having a liquid impermeable, garment-side layer, a liquid impermeable, body-side layer, and an absorbent layer disposed between the garment-side layer and the body-side layer. The absorbent body can be adapted for receiving a penis of a wearer between the body-side layer and the absorbent. The disposable absorbent device can also include a pouch adapted for receiving the scrotum of a wearer extending from the body-side layer. The absorbent device can also include a perimeter seal bonding at least a portion of the garment-side layer, the body-side layer and the pouch together. The perimeter seal can extend continuously, proximate the outer perimeters of the body-side layer and the garment-side layer.

17 Claims, 7 Drawing Sheets

(56) References Cited

U.S. PATENT DOCUMENTS

| | | |
|---|---|---|
| 7,927,320 B2 | 4/2011 | Goldwasser et al. |
| 2007/0043329 A1 | 2/2007 | Evans |
| 2008/0243097 A1 | 10/2008 | Goss |
| 2009/0270822 A1 | 10/2009 | Medeiros |
| 2009/0281510 A1 | 11/2009 | Fisher |

* cited by examiner

INCONTINENCE DEVICE FOR AMBULATORY MALES

FIELD OF THE INVENTION

The present invention relates generally to a disposable incontinence device for ambulatory males.

BACKGROUND

Urinary incontinence is a significant problem that has the potential to be very embarrassing for the individual suffering from the condition. Those who suffer from urinary incontinence run the spectrum from highly active to incapacitated. Regardless, those enduring urinary incontinence require solutions that allow them to live their lives with minimal disruption from this condition.

The myriad of absorbent devices designed to assist those with urinary incontinence suffer from any number of deficiencies, including being too bulky for active individuals and being indiscrete. The issue of discretion is particularly acute for males, especially when the need to change the absorbent device arises in public. Thus, there is a need for an improved disposable absorbent device for ambulatory males.

SUMMARY OF THE INVENTION

A disposable absorbent device for collecting urine from an individual is described. The disposable absorbent device can include an absorbent body, having a garment-side layer, a body-side layer, and an absorbent layer disposed between the liquid impermeable, garment-side layer and the liquid impermeable, body-side layer. The absorbent body can be adapted for receiving a penis of a wearer between the body-side layer and the absorbent. The disposable absorbent device can also include a pouch that is adapted for receiving the scrotum of a wearer and extends from the body-side layer. The disposable absorbent device can also include a fastening system coupled to an upper portion of the absorbent body.

The absorbent device can also include a perimeter seal bonding at least a portion of the garment-side layer, the body-side layer and the pouch together. The perimeter seal can extend continuously, proximate the outer perimeters of the body-side layer and the garment-side layer.

The pouch can include a secured edge and a free edge. The perimeter seal can bond the garment-side layer, the body-side layer and the secured edge together. The free edge of the pouch can extend from a first side edge of the absorbent body to a second side edge of the absorbent body. The length of the free edge can be longer than a distance from a first side transition to a second side transition of the pouch as attached to the absorbent body. The pouch can include an elastic portion proximate the free edge.

The secured edge can be generally arcuate. The free edge can include a generally arcuate intermediate portion and a length of the secured edge can be longer than a length of the generally arcuate intermediate portion.

The body-side layer can include a penile opening adapted for receiving a penis of a wearer. A height of said penile opening can be greater than a width of the penile opening. The body-side layer can include the penile opening therein. In some examples, the penile opening can be defined by a free edge of the body-side layer and the absorbent layer or the fluid management layer.

The absorbent body can also include a fluid management layer. In such devices, the absorbent layer can be disposed between the fluid management layer and the garment-side layer. The absorbent body can be adapted for receiving a penis of a wearer between the body-side layer and the fluid management layer. The perimeter seal can bond at least a portion of the garment-side layer, the body-side layer, the fluid management layer, and the pouch together.

These and other features, objects and advantages of the present invention will become more apparent to one skilled in the art from the following description and claims when read in light of the accompanying drawings.

DETAILED DESCRIPTION

Disposable absorbent devices for containing urine from an individual are described. The absorbent devices are designed to be used discretely, particularly with respect to leakage prevention and ease of donning and disposal. For example, because the disposable absorbent devices anchor at the scrotum and the waist of the user, the absorbent devices described herein can be easily donned and removed without needing to remove the pants, shorts or underwear or the user.

As shown in FIGS. 1-9, the disposable absorbent device 10 for containing urine voided by an individual, can include an absorbent body 12 and a pouch 14 extending from the absorbent body 12. The pouch 14 can be adapted for receiving a scrotum (S) of a wearer. The absorbent body 10 can include a liquid impermeable, garment-side layer 16; a liquid impermeable, body-side layer 18; and one or more absorbent layers 20 disposed between the garment-side layer 16 and the body-side layer 18. The absorbent body 12 can be adapted for receiving a penis (P) of a wearer between the body-side layer 18 and the absorbent 20.

The garment-side layer 16 and body-side layer 18 can both be impermeable to liquid to prevent leakage of fluid contained within the interior portion 42 of the absorbent body 12. The garment-side layer 16 and body-side layer 18 can both be vapor permeable so that the layers 16, 18 are breathable when worn. This enhances comfort of the wearer and the perception of dryness. Exemplary materials for the garment-side layer 16 and the body-side layer 18 include, but are not limited to, laminates comprising one or more of spunbond, melt blown and film. Such laminates are well known for making disposable personal care products, such as diapers, training pants, incontinence products, and feminine care products.

The absorbent layer(s) 20 can be made of any absorbent capable of containing urine. The absorbent layers 20 can be formed of mixtures of fiberized pulp and superabsorbent polymers capable of wicking urine and retaining the urine under pressure. For example, in some absorbent layers the pulp can provide for wicking, while the superabsorbent polymers can swell to form a gel that retains the urine even under pressure experienced during use. Exemplary absorbent layers 20 include both stabilized absorbent layers, such as airlaid materials, and unstabilized absorbent layers, such as the densified, fiberized pulp-superabsorbent polymer materials used as diaper absorbents.

As is evident from FIGS. 2, 3, 6, 8 & 9, the absorbent layer 20 can be contained within the absorbent body 12. As such, the perimeter of the absorbent layers 20 can fit completely within the perimeter of the garment-side layer 16, the body-side layer 18 and, where applicable, the fluid management layer 44. Thus, in some devices, the perimeter seal 22 can include at least some portion of the pouch 14, the garment-side layer 16, the fluid management layer 44 and the body-side layer 18. In some devices, no portion of the absorbent layer 20 is included in the perimeter seal 22. Because the absorbent is somewhat unstable and includes pulp, this arrangement can ensure that the perimeter seal 22 is fluid impermeable to prevent leakage.

As shown in FIGS. 3A, 3B, 5 & 6, the absorbent body 12 can also include a fluid management layer 44, with the absorbent layer 20 being disposed between the fluid management layer 44 and the garment-side layer 16. The fluid management layer 44 can provide for rapid intake of fluid, e.g., urine, as well as, distribution of fluid.

Figure 10:
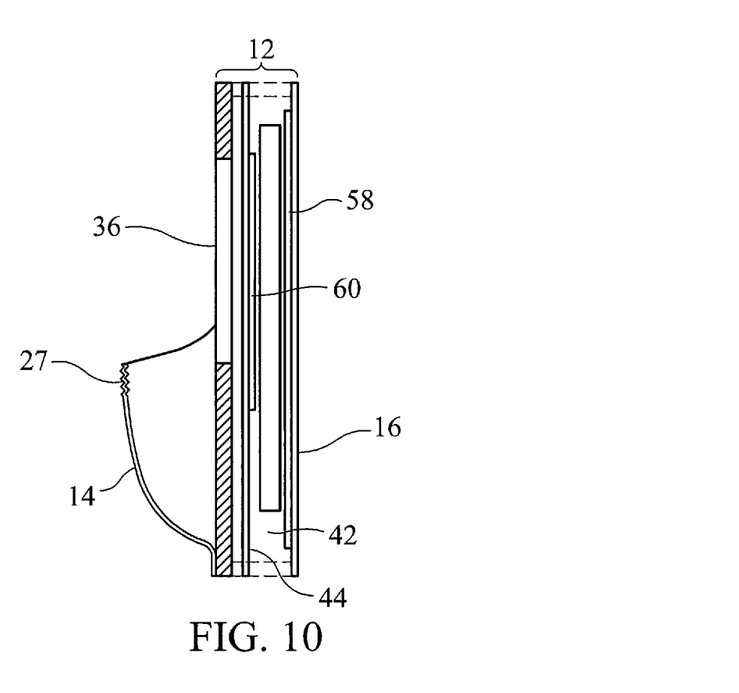
FIG. 10 is an exploded, cross-sectional view of the device shown in FIG. 7 having a spacer layer and a surge layer, taken along cut-line 8-8.

Of course, additional layers may optionally be included in the absorbent body 12. As shown in FIG. 10, the additional layers include a spacer layer 58, e.g., a breathable film, between the absorbent layer 20 and the garment-side layer 16; and a surge layer 60, e.g., a bonded-carded web, between the absorbent layer 20 and the fluid management layer 44. In some devices, a portion of the spacer layer 58, the surge layer 60, or both can be included in the perimeter seal 22. However, in other devices, neither the spacer layer 58 nor the surge layer 60 are included in the perimeter seal 22. The spacer layer 58 can be bonded to the garment-side layer 16. The surge 60 can be bonded to the fluid management layer 44.

The absorbent body 12 can be adapted for receiving a penis (P) of a wearer between the body-side layer 18 and the fluid management layer 44. As such, the fluid management layer 44 can be adapted to provide separation between the penis (P) of the wearer and the absorbent 20 in order to enhance a perception of dryness for the wearer.

The fluid management layer 44 can be a polymeric material with a hydrophilic coating. Exemplary materials for a fluid management layer include, but are not limited to, spunbond, melt blown, bonded-carded webs and perforated films.

The disposable absorbent device 10 can also include a perimeter seal 22 bonding at least a portion of the garment-side layer 16, the body-side layer 18, and the pouch 14 together. The perimeter seal 22 can extend continuously, proximate outer perimeters of the body-side layer 18 and the garment-side layer 16, as well as, a portion of the outer perimeter of the pouch 20.

In disposable absorbent devices 10 that include a fluid management layer 44, the perimeter seal 22 can bond at least a portion of the garment-side layer 16, the body-side layer 18, the fluid management layer 44 and the pouch 14 together. The perimeter seal 22 can extend continuously, proximate outer perimeters of the body-side layer 18, the fluid management layer 44, and the garment-side layer 16, as well as, a portion of the outer perimeter of the pouch 20. Regardless of the layers being bonded together, the perimeter seal 22 can be achieved using adhesives, thermal bonding, ultrasonic bonding, combinations thereof, or any other technique useful for forming a liquid impermeable seal.

The pouch 14 can be positioned so that it extends from the body-side layer 18. The pouch 14 can have a secured edge 24 and a free edge 26. The secured edge 24 can be coupled to the absorbent body 12. The perimeter seal 22 can bond together the garment-side layer 16, the body-side layer 18, the secured edge 24 and, where applicable, the fluid management layer 44.

The free edge 26 can extend from a first side 28 of the absorbent body 12 to a second side 30 of the absorbent body 12 opposite the first side 28. The first and second sides 28, 30 can be opposite lateral halves of the absorbent body 12.

Figure 4:
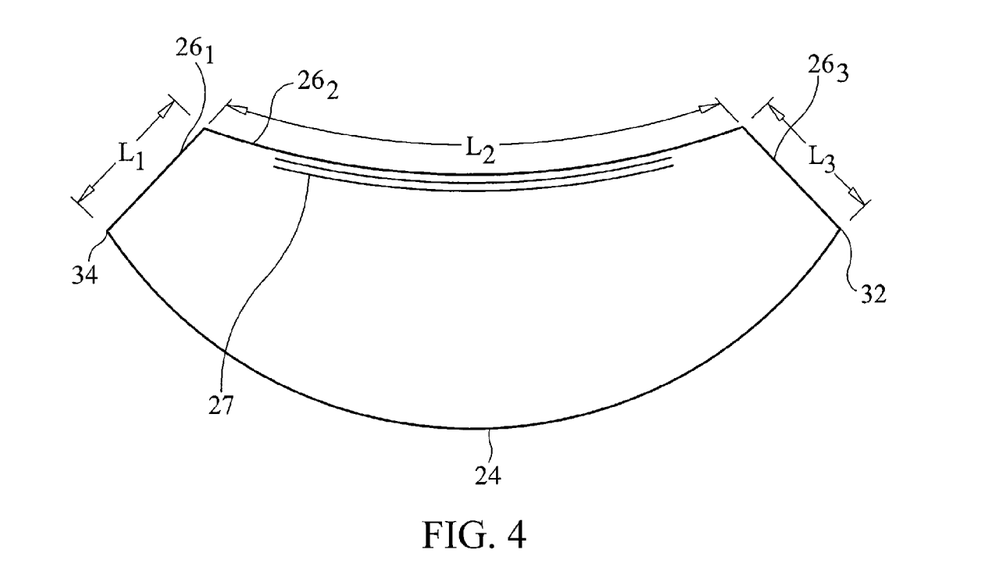
FIG. 4 is a plane view of an exemplary pouch prior to attachment to the absorbent device.

As best shown in FIG. 4, the secured edge 24 can be generally arcuate. The free edge 26 can also be generally arcuate. The free edge 26 can also include a generally arcuate intermediate portion between straight portions, as shown in FIG. 4. A length of the secured edge 24 can be longer than a length of the generally arcuate intermediate portion of the free edge 26.

The pouch 14 can include an elastic portion 27 proximate the free edge 26. For example, the elastic portion 27 can be one or more strands of elastomer attached to the pouch 14 proximate the free edge 26. Similarly, the elastomer can be in the form of an elastomeric film or non-woven coupled to the pouch 14 proximate the free edge 26. The properties, position and form of the elastomer can be selected to enable the pouch to securely couple to a scrotum of a user to anchor the base of the absorbent article 10.

A length (L) of the free edge 26 can be longer than a distance (d) from the first side transition 32 to the second side transition 34 of the absorbent device 10, i.e., after the pouch 14 is attached to the absorbent body 12. The side transitions 32, 34 are the intersections of the free edge 26 and the secured edge 24.

As used herein, the length (L) of the free edge 26 is the continuous length of the free edge 26 between the first and second side transitions 32, 34 of the pouch 14. The length is measured with any elastic portions of the pouch extended, so the presence or absence of an elastic portion does not impact the length of the free edge 26.

As shown in FIG. 4, the free edge 26 can include more than one side ($26_1 \ldots 26_n$). In such instances, the length (L) of the free edge 26 is the sum of the length of the sides ($\Sigma L_n$) of the free edge 26. The length (L) of the free edge 26 can be at least 125% of the distance (d), or at least 133% of the distance (d), or at least 150% of the distance (d), or at least 166% of the distance (d), or 175% of the distance (d), or at least 200% of the distance (d).

As shown in FIGS. 1-3 and 5-9, the absorbent body 12 can include a penile opening 36 adapted for receiving a penis of a wearer. The lower, interior portion 42 of the absorbent body 12 can provide a reservoir function when larger surges of urine are voided into the absorbent body 12 during an incidence of incontinence. This reservoir function provides additional time for fluid uptake by the absorbent 20 and reduces the likelihood of leakage while the urine is being absorbed by the absorbent 20, e.g., absorbed by a superabsorbent polymer or gelling agent.

In use, the body-side layer 18 can be positioned so that the penis (P) of the wearer can be positioned on one side of the body-side layer 18, while the scrotum (S) of the user is positioned on the opposite side. In general, the penis (P) of the wearer will not extend to the base 40 of the absorbent body 12. Because of this arrangement, it is possible for the lower, interior portion 42 of the absorbent body 12 to provide a reservoir function to manage surges of urine while keeping both the penis (P) and scrotum (S) of the wearer dry. In addition, the pouch 14 provides for a comfortable mechanism for anchoring the absorbent device 10 that enables the absorbent device 10 to be donned and removed by pulling down the users pants, but not removing them.

Figure 1:
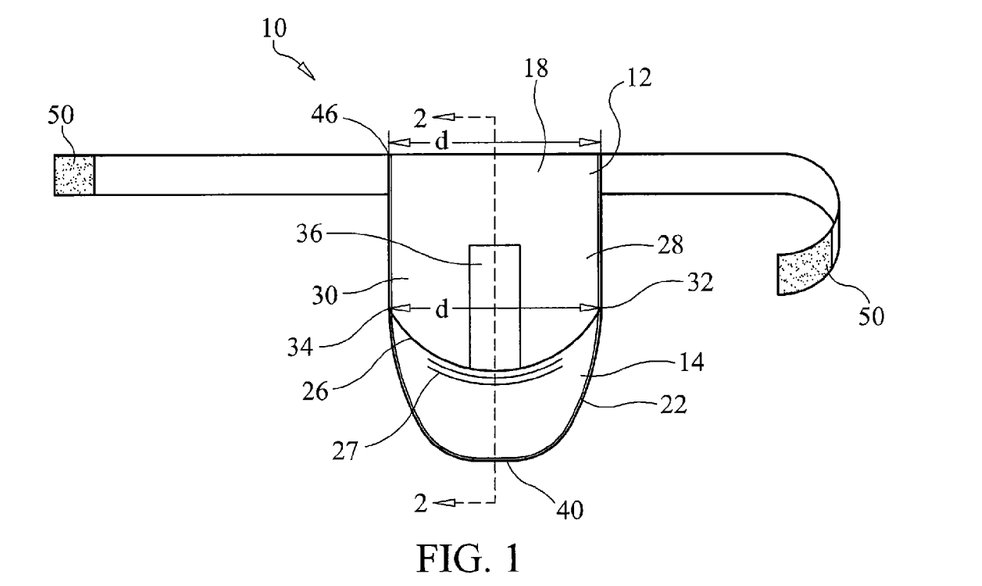
FIG. 1 is a perspective, rear view of a disposable absorbent device as described herein.
Figure 2A:
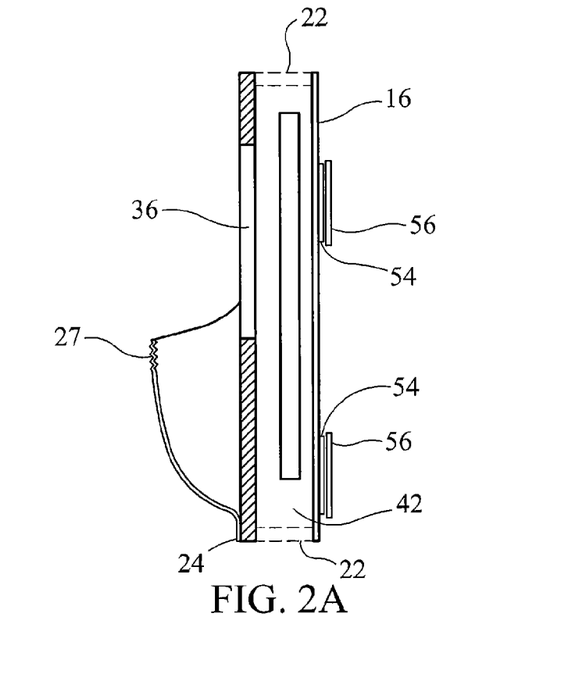
FIGS. 2A and 2B are exploded, cross-sectional views of the device shown in FIG. 1 taken along cut-line 2-2, prior to use and during use, respectively.
Figure 2B:
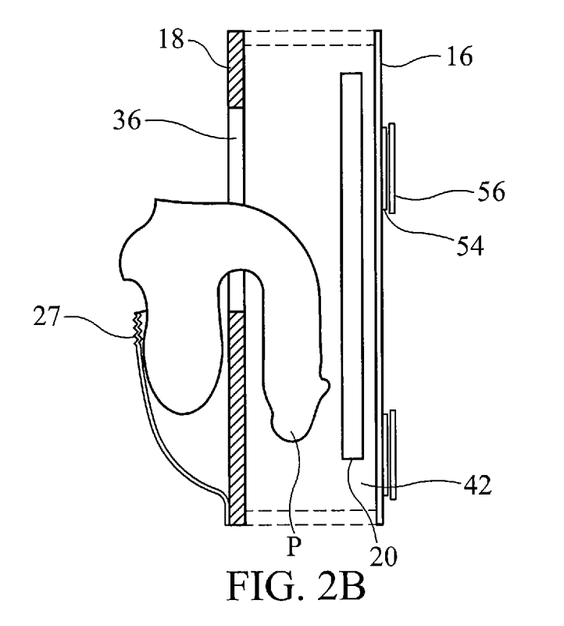
Figure 3A:
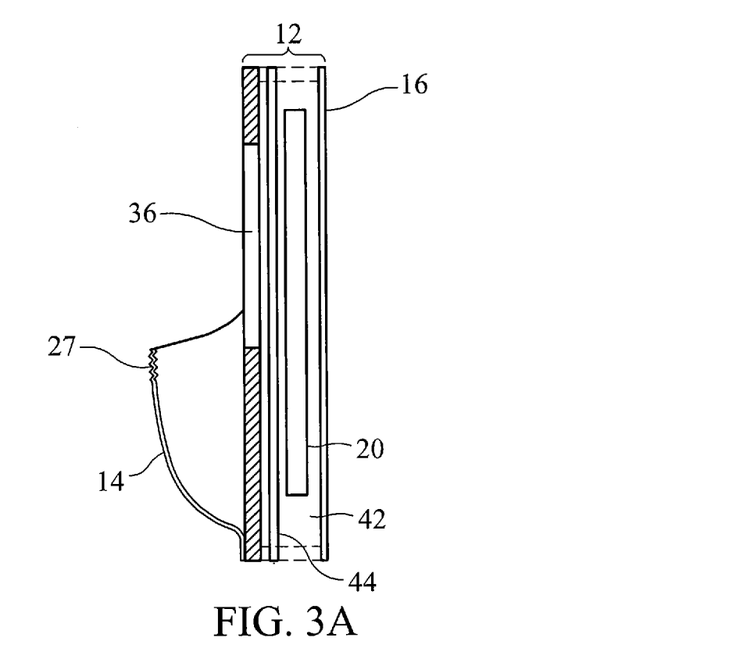
FIGS. 3A and 3B are exploded, cross-sectional views of the device shown in FIG. 1, including a fluid management layer, taken along cut-line 2-2, prior to use and during use, respectively.
Figure 3B:
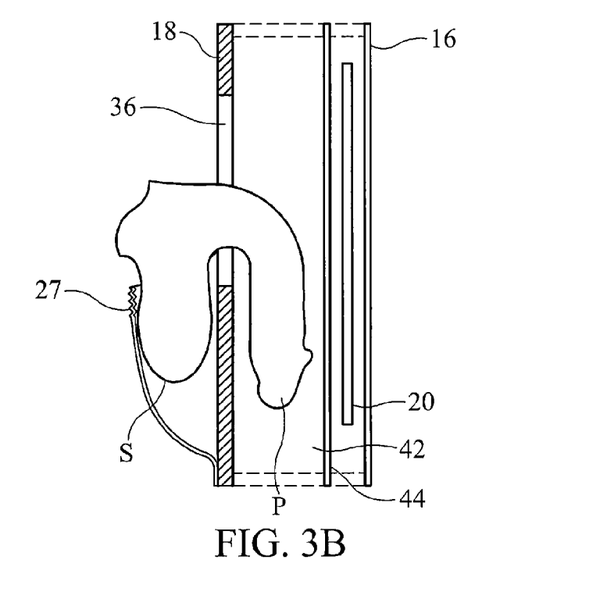
Figure 11:
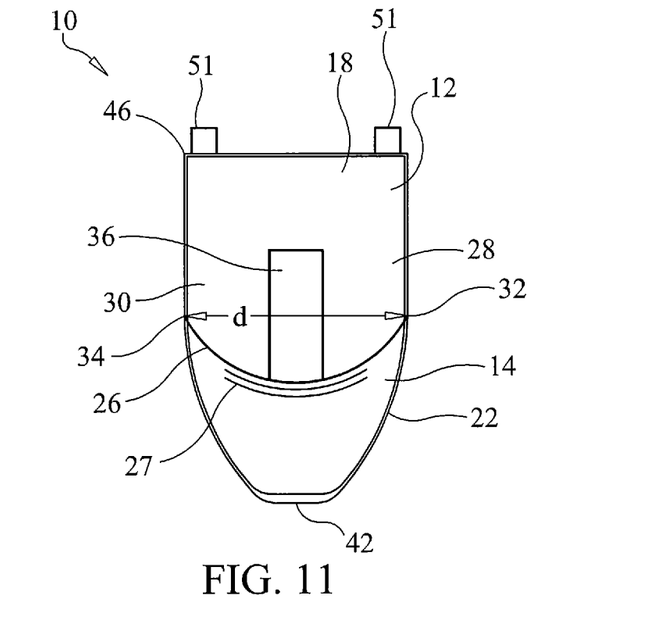
FIG. 11 is a perspective, rear view of a disposable absorbent device having a generally triangular base, as described herein.

As shown in FIG. 1, the absorbent body 12 can have a generally rectangular shape with a circular or elliptical portion proximate the base 40. Similarly, as shown in FIG. 11, the absorbent body 12 can have a generally rectangular shape with a generally triangular portion proximate the base 40. Because the absorbent device 10 is anchored using the scrotum of the user, it can be useful for the absorbent body 12 to become narrower proximate the base 40 in order to prevent discomfort, e.g., chaffing. Thus, the width ($W_b$) of the absorbent body 12 at the base 40 can be less than 75% of the width ($W_{mid}$) at the mid-point of the absorbent body 12. In some devices, the base width ($W_b$) can be less than 50%, or less than 25%, or less than 10% of the mid-point width ($W_{mid}$).

As shown in FIG. 1, the body-side layer 18 can include a penile opening 36 therein. A height of the penile opening 36 can be greater than a width of the penile opening 36. Such an arrangement may provide both improved retention of urine when the user moves or reclines in a supine position, as well as, improved control of the positioning of the penis (P) of the user while the absorbent device is being worn.

Figure 5:
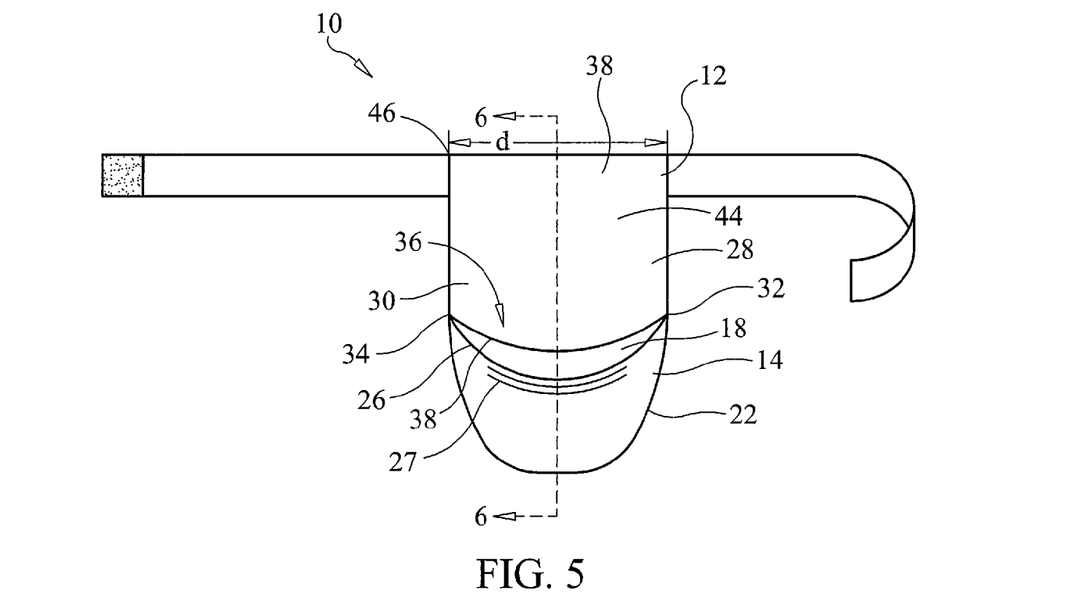
FIG. 5 is a perspective, rear view of a disposable absorbent device, including a partial body-side layer, as described herein.
Figure 6:
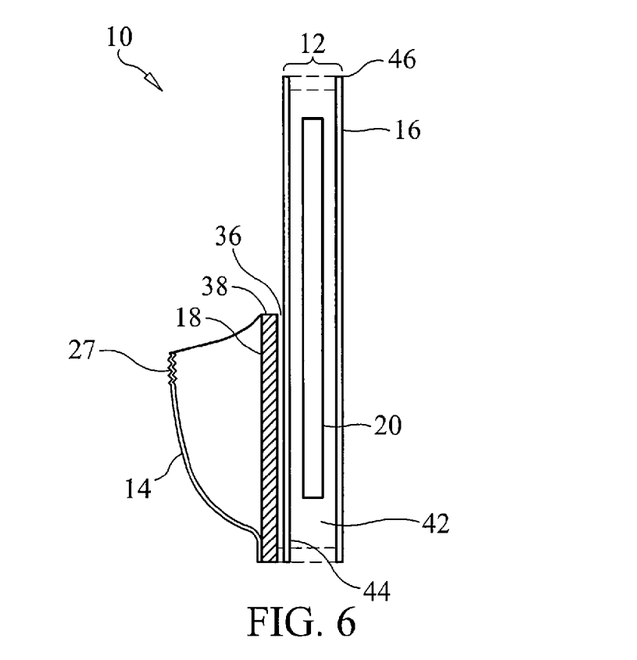
FIG. 6 is an exploded, cross-sectional view of the device shown in FIG. 5 taken along cut-line 6-6.

As shown in FIG. 5, the penile opening 36 can be defined by a free edge 38 of the body-side layer 18 and the fluid management layer 44 or by the free edge 38 of the body-side layer 18 and the absorbent layer 20. In such embodiments, the body-side layer 18 does not extend to the top 46 of the absorbent body 12, but still extends high enough to provide a reservoir function and separate the scrotum (S) of the wearer from the interior 42 of the absorbent body.

The disposable absorbent device 10 can also include a fastening system coupled to an upper portion of the absorbent body 12. For example, as shown in FIGS. 1 & 5, a belt 48 can be attached to the absorbent body for securing around the waist of the wearer. The belt 48 can include one or more straps and be made adjustable using a variety of fastening devices 50, including but not limited to hook-and-loop material and adhesive. The belt 48 can be permanently coupled to the absorbent body 12 or can be reusable.

Figure 7:
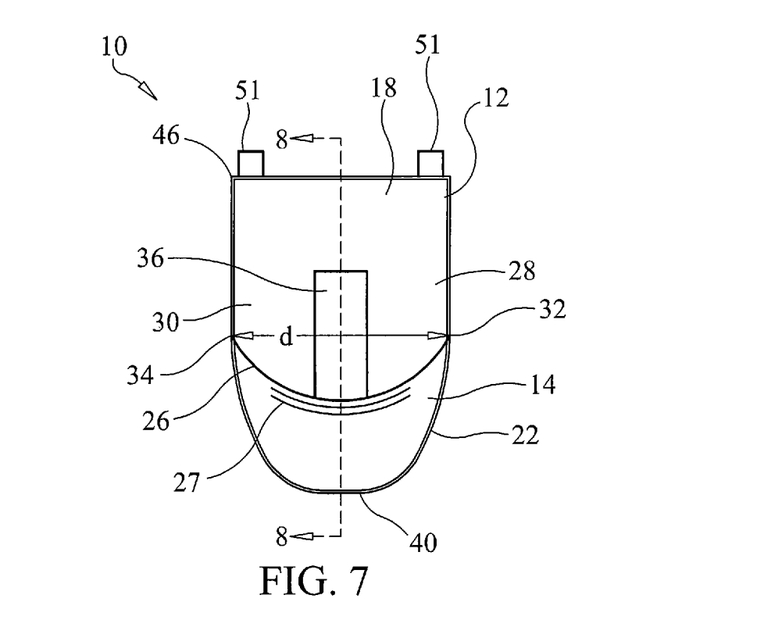
FIG. 7 is a perspective, rear view of a disposable absorbent device, including a hook attachment mechanism, as described herein.
Figure 8:
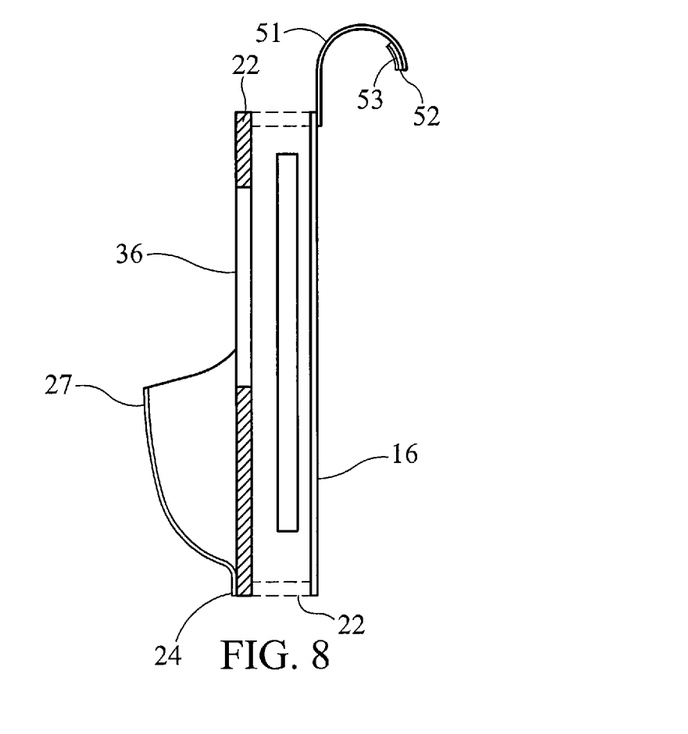
FIG. 8 is an exploded, cross-sectional view of the device shown in FIG. 7, having a flexible hook, taken along cut-line 8-8.
Figure 9:
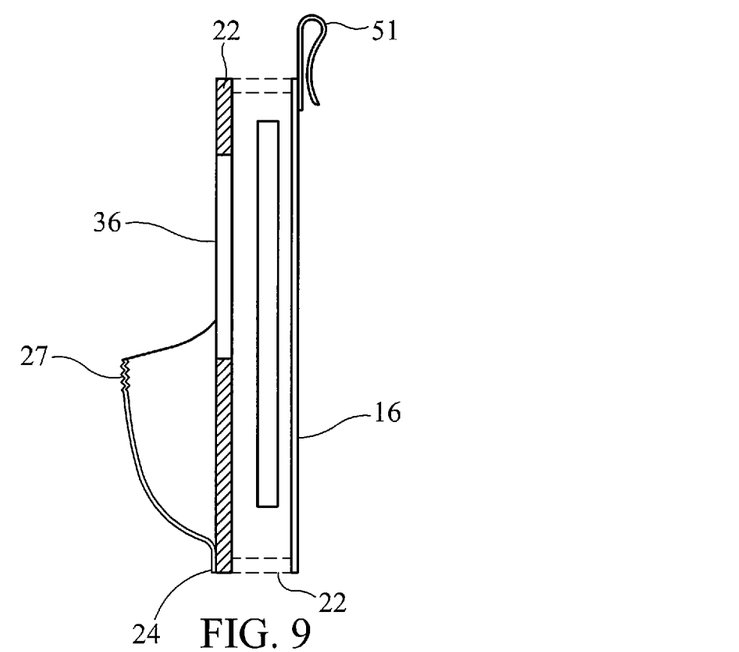
FIG. 9 is an exploded, cross-sectional view of the device shown in FIG. 7, having a resilient hook, taken along cut-line 8-8.

As shown in FIGS. 7-9, the upper portion of the absorbent body 12 can alternately or also include hooks 51 or other devices for attaching to the waistband of the user's underwear, shorts, or pants. The hooks 51 can be a molded clips, strips of material, e.g., a non-woven, with adhesive 52 at the end, or any other securing mechanism that can hook over and secure to the user's underwear, shorts or pants. Where adhesive 52 is used, the adhesive 52 can be covered with a peel strip 53.

The garment-side layer 16 can also include adhesive material 54 covered with a peel strip 56 to secure the absorbent body 12 to the user's underwear, e.g., briefs. Any and all of the fastening approaches described herein can be used independently or in combination.

The foregoing is provided for purposes of illustrating, explaining, and describing embodiments of this invention. Modifications and adaptations to these embodiments will be apparent to those skilled in the art and may be made without departing from the scope or spirit of this invention.

What is claimed is:

1. A disposable absorbent device for collecting urine from an individual, comprising:
    an absorbent body, comprising:
        a liquid impermeable, garment-side layer,
        a liquid impermeable, body-side layer, and
        an absorbent layer disposed between said garment-side layer and said body-side layer, wherein said absorbent body is adapted for receiving a penis of a wearer between said body-side layer and said absorbent;
    a pouch extending from said body-side layer, said pouch adapted for receiving a scrotum of a wearer; and
    a perimeter seal bonding said garment-side layer, said body-side layer and a secured edge of said pouch together, wherein said perimeter seal extends continuously, proximate entire outer perimeters of said body-side layer and said garment-side layer to prevent fluid leakage from an interior of the absorbent body.

2. The disposable absorbent device according to claim 1, wherein said pouch comprises the secured edge and a free edge and said perimeter seal bonds said garment-side layer, said body-side layer and said secured edge together.

3. The disposable absorbent device according to claim 1, wherein said pouch comprises a secured edge coupled to said absorbent body and a free edge.

4. The disposable absorbent device according to claim 3, wherein said free edge extends from a first side edge of said absorbent body to a second side edge of said absorbent body.

5. The disposable absorbent device according to claim 4, wherein a length of said free edge is longer than a distance from a first side transition to a second side transition of the pouch as attached to the absorbent body.

6. The disposable absorbent device according to claim 3, wherein said pouch comprises an elastic portion proximate said free edge.

7. The disposable absorbent device according to claim 3, wherein said secured edge is generally arcuate, said free edge comprises an generally arcuate intermediate portion, and a length of said secured edge is longer than a length of said generally arcuate intermediate portion.

8. The disposable absorbent device according to claim 1, wherein said body-side layer comprises a penile opening adapted for receiving a penis of a wearer.

9. The disposable absorbent device according to claim 8, wherein a height of said penile opening is greater than a width of said penile opening.

10. The disposable absorbent device according to claim 8, wherein said body-side layer comprises said penile opening.

11. The disposable absorbent device according to claim 8, wherein said penile opening is defined by a free edge of said body-side layer and said garment-side layer.

12. The disposable absorbent device according to claim 1, further comprising a fastening system coupled to an upper portion of said absorbent body.

13. The disposable absorbent device according to claim 1, wherein said absorbent body further comprises a fluid management layer, said absorbent layer being disposed between said fluid management layer and said garment-side layer.

14. The disposable absorbent device according to claim 13, wherein said absorbent body is adapted for receiving a penis of a wearer between said body-side layer and said fluid management layer.

15. The disposable absorbent device according to claim 13, further comprising a perimeter seal, bonding at least a portion of said garment-side layer, said fluid management layer, said body-side layer, and said pouch together.

16. A disposable absorbent device for collecting urine from an individual, comprising:
 an absorbent body, comprising:
  a liquid impermeable, garment-side layer,
  a liquid impermeable, body-side layer,
  an absorbent layer disposed between said garment-side layer and said body-side layer, and
  a fluid management layer, wherein said absorbent layer is disposed between said fluid management layer and said garment-side layer and said absorbent body is adapted for receiving a penis of a wearer between said body-side layer and said fluid management layer;
 a pouch extending from said body-side layer, said pouch adapted for receiving a scrotum of a wearer; and
 a perimeter seal bonding said garment-side layer, said body-side layer and a secured edge of said pouch together, wherein said perimeter seal extends continuously, proximate entire outer perimeters of said body-side layer and said garment-side layer to prevent fluid leakage from an interior of the absorbent body.

17. The disposable absorbent device according to claim 16, wherein said pouch comprises the secured edge and a free edge and said perimeter seal bonds said garment-side layer, said fluid management layer, said body-side layer and said secured edge together.

* * * * *